(12) United States Patent　　(10) Patent No.: US 8,814,802 B2
　Iijima et al.　　　　　　　　　　　　(45) Date of Patent:　　Aug. 26, 2014

(54) BIOLOGICAL INFORMATION DETECTOR AND BIOLOGICAL INFORMATION MEASURING DEVICE

(75) Inventors: Yoshitaka Iijima, Nagano (JP); Hideto Yamashita, Nagano (JP); Hideo Miyasaka, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 197 days.

(21) Appl. No.: 12/979,496

(22) Filed: Dec. 28, 2010

(65) Prior Publication Data

US 2011/0166462 A1　Jul. 7, 2011

(30) Foreign Application Priority Data

Jan. 5, 2010　(JP) ................... 2010-000452

(51) Int. Cl.
*A61B 5/02*　　(2006.01)

(52) U.S. Cl.
USPC ............ 600/500; 600/473; 600/476; 600/503

(58) Field of Classification Search
USPC .......................... 600/324, 344, 500, 502, 503
See application file for complete search history.

(56) References Cited

U.S. PATENT DOCUMENTS

| | | | |
|---|---|---|---|
| 4,685,464 A * | 8/1987 | Goldberger et al. | 600/344 |
| 2005/0075549 A1 * | 4/2005 | Kondoh et al. | 600/323 |
| 2005/0253047 A1 | 11/2005 | Maegawa et al. | |
| 2008/0097221 A1 | 4/2008 | Florian | |
| 2008/0277679 A1 * | 11/2008 | Akimoto | 257/94 |
| 2010/0056887 A1 * | 3/2010 | Kimura et al. | 600/324 |

FOREIGN PATENT DOCUMENTS

| | | |
|---|---|---|
| JP | 2002-048637 A | 2/2002 |
| JP | 2004-333179 A | 11/2004 |
| JP | 2004-337605 A | 12/2004 |
| JP | 2005-323906 A | 11/2005 |
| JP | 2009-207713 A | 9/2009 |

* cited by examiner

*Primary Examiner* — Navin Natnithithadha
*Assistant Examiner* — Etsub Berhanu
(74) *Attorney, Agent, or Firm* — Global IP Counselors, LLP

(57) ABSTRACT

A biological information detector including a light-emitting part for emitting a light directed at a detection site of a test subject, a light-receiving part for receiving a light having biological information, the light produced by the light emitted by the light-emitting part being reflected at the detection site, a reflecting part for reflecting the light emitted by the light-emitting part or the light having biological information, a protecting part, having a transparent surface in contact with the test subject, for protecting the light-emitting part or the light-receiving part, and a substrate held between the reflecting part and the protecting part, the light-emitting part being positioned on a side of the substrate towards one of either the reflecting part or the protecting part, and the light-receiving part being positioned on a side of the substrate towards another of either the reflecting part or the protecting part.

9 Claims, 13 Drawing Sheets

(A)

(B)

(C)

BIOLOGICAL INFORMATION DETECTOR AND BIOLOGICAL INFORMATION MEASURING DEVICE

BACKGROUND

1. Technological Field

The present invention relates to a biological information detector and a biological information measuring device and similar devices.

2. Background Technology

A biological information measuring device measures human biological information such as, for example, pulse rate, blood oxygen saturation level, body temperature, or heart rate, and an example of a biological information measuring device is a pulse rate monitor for measuring the pulse rate. Also, a biological information measuring device such as a pulse rate monitor may be installed in a clock, a mobile phone, a pager, a PC, or another electrical device, or may be combined with the electrical device. The biological information measuring device has a biological information detector for detecting biological information, and the biological information detector includes a light-emitting part for emitting light towards a detection site of a test subject (a user), and a light-receiving part for receiving light having biological information from the detection site.

In Patent Citation 1, there is disclosed a pulse rate monitor (or in a broader sense, a biological information measuring device). A light-receiving part (e.g. a light-receiving part 12 in FIG. 16 of Patent Citation 1) of the pulse rate monitor receives light reflected at a detection site (e.g. dotted line in FIG. 16 of Patent Citation 1) via a diffusion reflection plane (e.g. reflecting part 131 in FIG. 16 of Patent Citation 1). In an optical probe 1 in Patent Citation 1, a light-emitting part 11 and the light-receiving part 12 overlap in plan view, and the size of the optical probe is reduced.

PRIOR ART REFERENCE

Patent Citation

Patent Citation 1: JP-A 2004-337605 is an example of related art.

SUMMARY

Problems to be Solved by the Invention

The light-emitting part 11 and the light-receiving part 12 in Patent Citation 1 are positioned, along with a substrate 15, in an interior of the reflecting part 131, and the interior of the reflecting part 131 is filled with a transparent material 142. Although a configuration of such description makes it possible to reduce the size of the optical probe 1, the optical probe 1 cannot be assembled with ease.

According to several modes of the present invention, it is possible to provide a biological information detector and a biological information measuring device in which assembly is facilitated.

Means Used to Solve the Above-Mentioned Problems

A first aspect of the present invention relates to a biological information detector, characterized in comprising: a light-emitting part subjected to emit a light directed at a detection site of a test subject; a light-receiving part subjected to receive a light having biological information, the light produced by the light emitted by the light-emitting part being reflected at the detection site; a reflecting part subjected to reflect the light emitted by the light-emitting part or the light having biological information; a protecting part subjected to protect the light-emitting part or the light-receiving part; and a substrate, held between the reflecting part and the protecting part, the light-emitting part being positioned on a side of the substrate towards one of either the reflecting part or the protecting part, and the light-receiving part being positioned on a side of the substrate towards another of either the reflecting part or the protecting part; wherein the protecting part has a surface in contact with the test subject; the protecting part is formed from a material that is transparent with respect to a wavelength of the light emitted by the light-emitting part; and the substrate is formed from a material that is transparent with respect to the wavelength of the light emitted by the light-emitting part.

According to the first aspect of the present invention, the substrate is held between the reflecting part and the protecting part. Therefore, even in an instance in which the light-emitting part and the light-receiving part are positioned on the substrate, there is no need to separately provide a mechanism for supporting the substrate itself, and the number of components is smaller. Also, since the substrate is formed from a material that is transparent with respect to the emission wavelength, the substrate can be disposed on a light path from the light-emitting part to the light-receiving part, and there is no need to accommodate the substrate at a position away from the light path, such as in an interior of the reflecting part 18. A biological information detector that can be readily assembled can thus be provided.

According to a second aspect of the present invention, the substrate may have a first surface corresponding to a light transmission region, and a second surface that is opposite the second surface, and a light transmission film may be formed on at least one of the first surface and the second surface.

Coating the substrate with the light transmission film thus makes it possible to cover rough parts of a surface of the substrate and reduce diffusion of light off the surface roughness. In other words, the transmittance of the substrate can be increased. Therefore, the amount of light reaching the light-receiving part or the detection site increases, and the detection accuracy of the biological information detector further increases.

According to a third aspect of the present invention, the light transmission film may allow selective transmission of light emitted by the light-emitting part.

Reducing the amount of light other than that emitted by the light-emitting part (or in a broad sense, noise) thus further increases the detection accuracy of the biological information detector.

According to a fourth aspect of the present invention, the reflecting part may be secured to the substrate; the substrate may be a flexible substrate; and an end part of the substrate is capable of bending.

The reflecting part is thus secured to the substrate, and it is therefore possible to provide a biological information detector that can be readily assembled. Also, since the substrate is held between the reflecting part and the protecting part, even with a flexible substrate that inherently lacks stiffness, the light-emitting part and the light-receiving part can be mounted on the substrate and supported. Also, since the end part of the substrate to which the reflecting part is not secured is capable of bending, it is possible to provide a small biological information detector.

According to a fifth aspect of the present invention, the biological information detector may further comprise an infrared cut filter.

Since biological substances (water or hemoglobin) readily allow transmission of infrared light, the infrared cut filter makes it possible to reduce a noise component arising from external light.

According to a sixth aspect of the present invention, the biological information detector may further comprise a wristband capable of attaching the biological information detector to an arm of the test subject.

The detection site can thus be set on the arm of the test subject (i.e., the user).

A seventh aspect of the present invention relates to a biological information measuring device, characterized in comprising: the biological information detector described above; and a biological information measuring part for measuring biological information from a light reception signal generated at the light-receiving part.

According to the seventh aspect of the present invention, the biological information detector that can be readily assembled can be used to readily assemble the entire biological information measuring device.

According to an eighth aspect of the present invention, the biological information may be a pulse rate.

A biological information detector that can be readily assembled can thus be applied to a pulse rate monitor.

DESCRIPTION OF EXEMPLARY EMBODIMENTS

Figure 1:
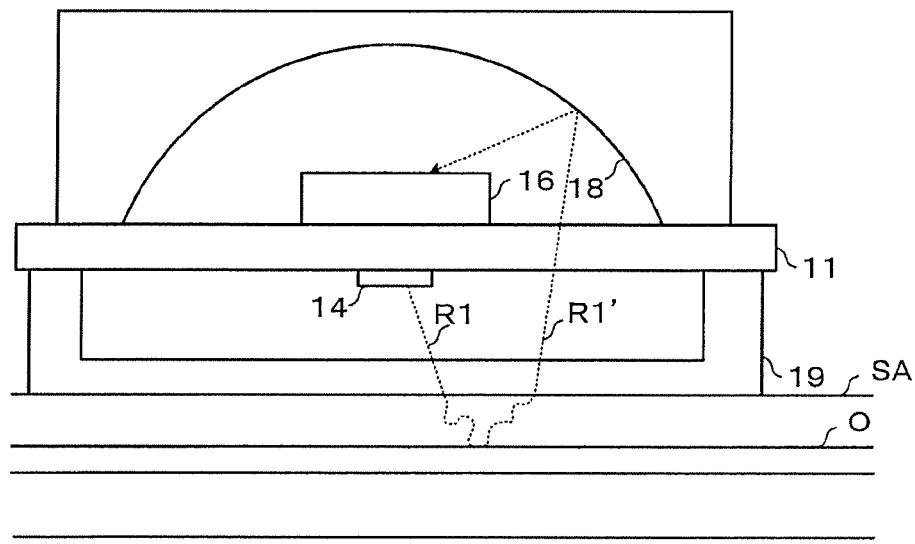
FIGS. 1(A) and 1(B) are examples of a configuration of a biological information detector according to a present embodiment.
Figure 1:
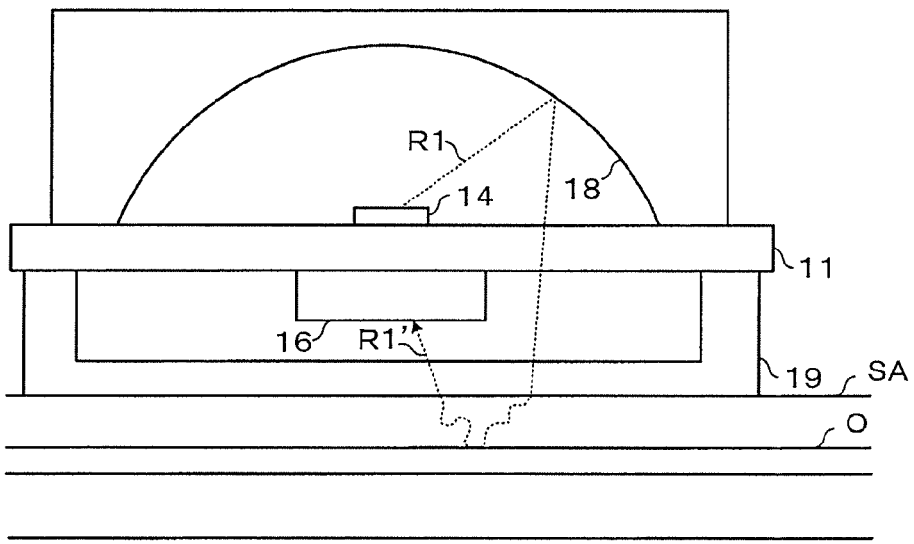

A description shall now be given for the present embodiment. The present embodiment described below is not intended to unduly limit the scope of the Claims of the present embodiment. Not every configuration described in the present embodiment is necessarily an indispensible constituent feature of the present invention.

1. Biological Information Detector

FIGS. 1(A) and 1(B) each show an example of a configuration of a biological information detector according to a present embodiment. As shown in FIGS. 1(A) and 1(B), the biological information detector contains a light-emitting part 14, a light-receiving part 16, a reflecting part 18, and a protecting part 19. The light-emitting part 14 emits a light R1 directed at a detection site O of a test subject (e.g. a user). The light-receiving part 16 receives a light R1' (i.e. a reflected light) having biological information, produced by the light R1 emitted by the light-emitting part 14 being reflected at the detection site O. The reflecting part 18 reflects the light R1 emitted by the light-emitting part 14 or the light R1' (i.e. the reflected light) containing the biological information. The reflecting part 18 may have a reflecting surface on a dome surface provided on a light path between the light-emitting part 14 and the light-receiving part 16. The protecting part 19 protects the light-emitting part 14 or the light-receiving part 16. In the example shown in FIG. 1(A), the protecting part 19 protects the light-emitting part 14. In the example shown in FIG. 1(B), the protecting part 19 protects the light-receiving part 16.

As shown in FIGS. 1(A) and 1(B), the biological information detector further contains a substrate 11. The substrate 11 is held between the reflecting part 18 and the protecting part 19, the light-emitting part 14 is positioned on a side of the substrate 11 towards one of either the reflecting part 18 or the protecting part 19, and the light-receiving part 16 is positioned on a side of the substrate 11 towards another of either the reflecting part 18 or the protecting part 19. In the example shown in FIG. 1(A), the light-receiving part 16 is placed on the side of the substrate 11 towards the reflecting part 18 (or specifically, a first surface of the substrate 11), and the light-emitting part 14 is placed on the side of the substrate 11 towards the protecting part 19 (or specifically, a second surface of the substrate 11). In the example shown in FIG. 1(B), the light-receiving part 14 is placed on the side of the substrate 11 towards the reflecting part 18 (i.e., the first surface), and the light-emitting part 16 is placed on the side of the substrate 11 towards the protecting part 19 (i.e., the second surface). The protecting part 19 has a contact surface in contact with the test subject, and the protecting part 19 is formed from a material that is transparent with respect to a wavelength of the light R1 emitted by the light-emitting part 14 (e.g. glass). The substrate 11 is also formed form a material that is transparent with respect to the wavelength of the light R1 emitted by the light-emitting part 14 (e.g. a polyimide).

Since the substrate 11 is held between the reflecting part 18 and the protecting part 19, even in an instance in which the light-emitting part 14 and the light-receiving part 16 is positioned on the substrate 11, there is no need to separately provide a mechanism for supporting the substrate 11 itself, and the number of components is smaller. Also, since the substrate 11 is formed from a material that is transparent with respect to the emission wavelength, the substrate 11 can be disposed on a light path from the light-emitting part 14 to the light-receiving part 16, and there is no need to accommodate the substrate 11 at a position away from the light path, such as within the reflecting part 18. A biological information detector that can be readily assembled can thus be provided. Also, the reflecting part 18 is capable of increasing the amount of light reaching the light-receiving part 16 or the detection site O, and the detection accuracy (i.e., the signal-to-noise ratio) increases.

In Patent Citation 1, it is necessary to install the light-emitting part 11, the light-receiving part 12, the substrate 15, and the transparent material 142 in the interior of the reflecting part 131. Therefore, a small optical probe 1 cannot be assembled with ease. Also, according to paragraph [0048] in Patent Citation 1, the substrate 15 is formed so that an interior-side of the reflecting part 131 is a diffuse reflection surface. In other words, the substrate 15 in Patent Citation 1 is not required to be formed from a transparent material.

In the examples shown in FIGS. 1(A) and 1(B), the detection site O (e.g. a blood vessel) is within the test subject. The first light R1 travels into the test subject, and diffuses or scatters at the epidermis, the dermis, and the subcutaneous tissue. Then, the first light R1 reaches the detection site O, and is reflected at the detection site O. The reflected light R1' reflected at the detection site O diffuses or scatters at the subcutaneous tissue, the dermis, and the epidermis. In FIG. 1(A), the reflected light R1' travels to the reflecting part 18. In FIG. 1(B), the light R1 travels to the detection site O via the reflecting part 18. The light R1 is partially absorbed at the blood vessel. Therefore, due to an effect of a pulse, the rate of absorption at the blood vessel varies, and the amount of the reflected light R1' reflected at the detection site O also varies. Biological information (e.g. pulse rate) is thus reflected in the reflected light R1' reflected at the detection site O.

In the example shown in FIG. 1(A), the light-emitting part 14 emits the first light R1 at the detection site O; the reflecting part 18 reflects the reflected light R1', produced by the first light R1 being reflected at the detection site O, at the light-receiving part 16; and the light-receiving part 16 receives the reflected light R1' containing the biological information at the detection site O. In the example shown in FIG. 1(B), the light-emitting part 14 emits the first light R1 at the detection site O via the reflecting part 18, and the light-receiving part 16 receives the reflected light R1', produced by the first light R1 being reflected, containing the biological information at the detection site O.

The thickness of the substrate 11 is e.g. 10 µm to 1000 µm. Wiring for the light-emitting part 14 and wiring for the light-receiving part 16 may be formed on the substrate 11. The substrate 11 is e.g. a printed circuit board; however, a printed circuit board is not generally formed from a transparent material, as with the substrate 15 of Patent Citation 1. Specifically, the inventors purposefully used a configuration in which the printed circuit board is formed from a material that is transparent at least with respect to the emission wavelength of the light-emitting part 14. The thickness of the protecting part 19 is e.g. 1 µm to 1000 µm.

Examples of configurations of the biological information detector are not limited by that shown in FIGS. 1(A) and 1(B), and the shape, or a similar attribute, of a part of the example of configuration (e.g. the light-receiving part 16) may be modified. The biological information may also be blood oxygen saturation level, body temperature, heart rate, or a similar variable; and the detection site O may be positioned at a surface SA of the test subject. In the example shown in FIGS. 1(A) and 1(B), the first light R1 is shown by a single line; however, in reality, the light-emitting part 14 emits many light beams in a variety of directions FIGS. 2(A), 2(B), and 2(C) respectively show an example of a configuration of the first reflecting part 12 shown in FIG. 1. As shown in FIG. 2(A), the first reflecting part 12 may have a support part 12-1 for supporting the light-emitting part 14, and an inner wall surface 12-2 and a top surface 12-3 of the wall part surrounding the second light-emitting surface 14B of the light-emitting part 14. In FIGS. 2(A) through 2(C), the light-emitting part 14 is omitted. In the example shown in FIG. 2(A), the first reflecting part 12 is capable of reflecting the second light R2 towards the detection site O off the inner wall surface 12-2 (see FIG. 1), and has the first reflecting surface on the inner wall surface 12-2. The thickness of the support part 12-1 is e.g. 50 µm to 1000 µm, and the thickness of the top surface 12-3 is e.g. 100 µm to 1000 µm. The first reflecting part 12 may not necessarily have the support part 12-1, and the light-emitting part 14 may be supported by a part other than the first reflecting part 12.

Figure 2:
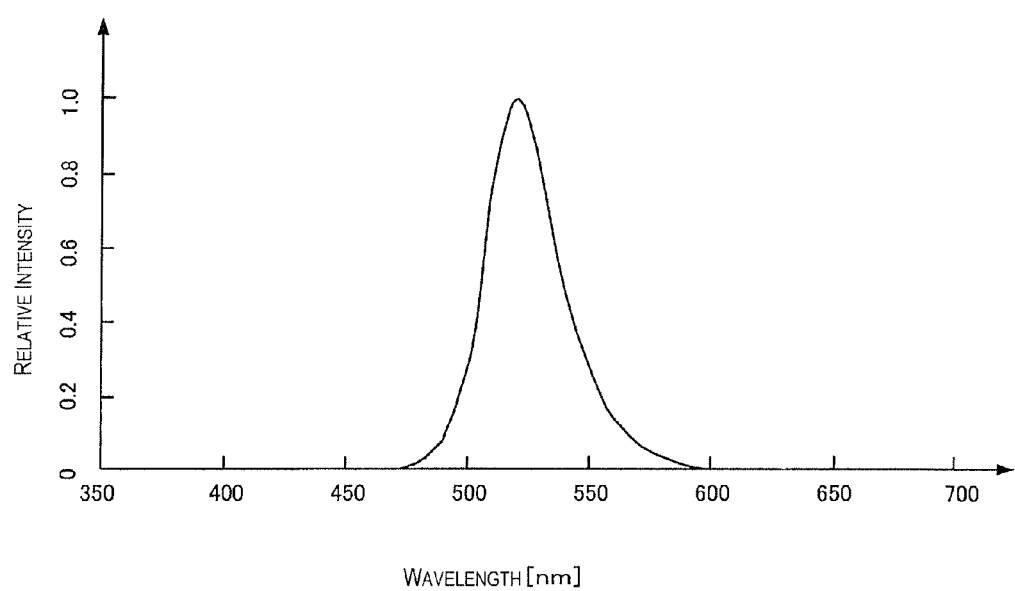
FIG. 2 is an example of intensity characteristics of light emitted by a light-emitting part.

FIG. 2 is an example of intensity characteristics of light emitted by the light-emitting part 14. In the example shown in FIG. 2, the intensity is at a maximum for light having a wavelength of 520 nm, and the intensity of light having other wavelengths is normalized with respect thereto. Also, in the example shown in FIG. 2, the wavelengths of light emitted by the light-emitting part 14 are within a range of 470 nm to 600 nm.

Figure 3:
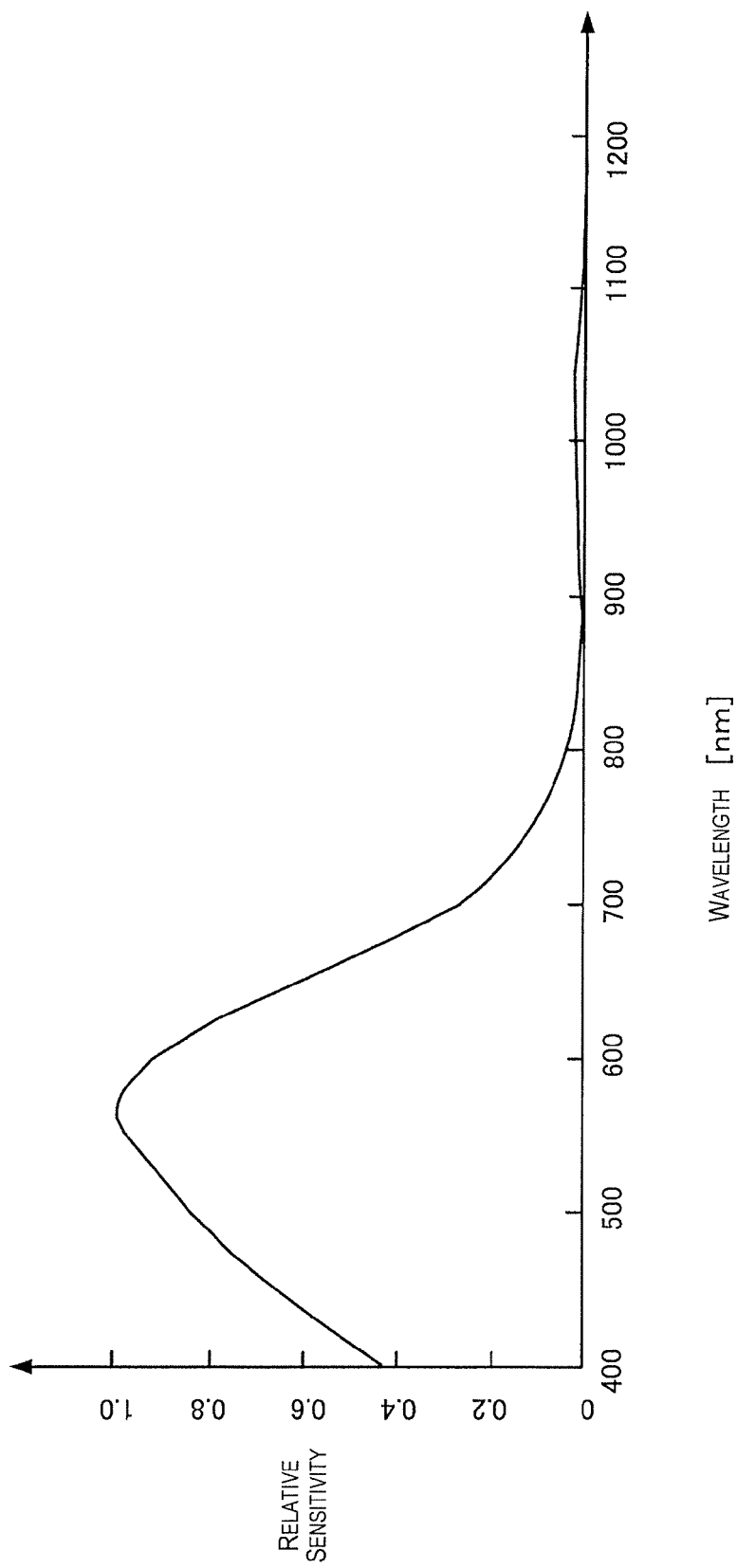
FIG. 3 is an example of sensitivity characteristics of light received by a light-receiving part.

FIG. 3 is an example of sensitivity characteristics of light received by the light-receiving part 16. In the example shown in FIG. 3, the sensitivity is at a maximum for light having a wavelength of 565 nm, and the sensitivity for light having other wavelengths is normalized with respect thereto. The wavelength of light received by the light-receiving part 16 at which the sensitivity is at the maximum, shown in FIG. 3, is within the range of wavelengths emitted by the light-emitting part 14 shown in FIG. 2, but is not within a range of 700 nm to 1100 nm, which is known as the biological window. In the example shown in FIG. 3, the sensitivity of infrared light falling within the range of 700 nm to 1100 nm is set at a relative sensitivity of 0.3 (i.e., 30%) or less. The wavelength of light received by the light-receiving part 16 at which the wavelength is at the maximum (e.g. 565 nm) is preferably closer to the wavelength at which the intensity of light emitted by the light-emitting part 14 is at the maximum (i.e., 520 nm) than a lower limit of the biological window (i.e., 700 nm).

Figure 4:
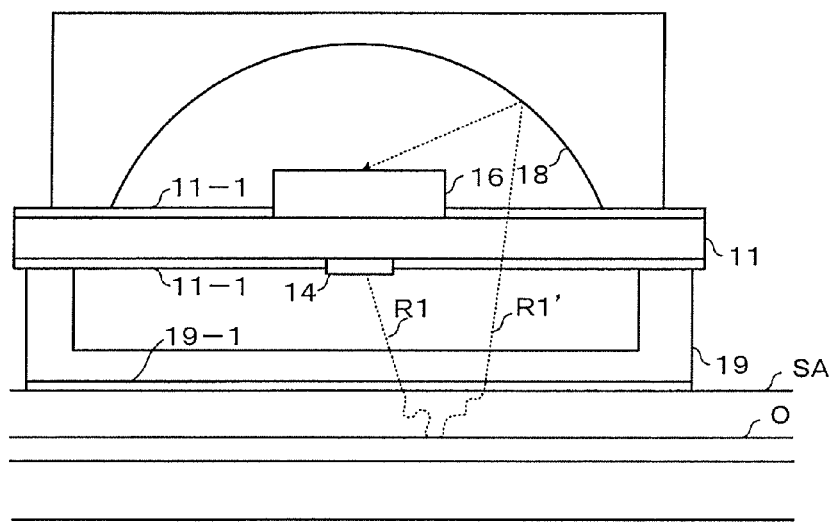
FIG. 4 is an example of another configuration of a biological information detector according to the present embodiment.

FIG. 4 is an example of another configuration of a biological information detector according to the present embodiment. As shown in FIG. 4, a light transmission film 11-1 can be formed on each of a first surface (e.g. a front surface) of a substrate 11 and a second surface (e.g. a reverse surface) that is opposite the first surface). Structures that are identical to those in the example described above are affixed with the same numerals, and a description of the structures will be omitted. The light transmission film 11-1 may also be formed only on the first surface, or formed only on the second surface. In the example shown in FIG. 4, the light transmission film 11-1 is formed on a light transmission region of the substrate 11 at which the light-emitting part 14 and the light-receiving part 16 are not positioned. Although FIG. 4 corresponds to FIG. 1(A), the light transmission film 11-1 may also be formed on at least one of the first surface and the second surface of the substrate 11 shown in FIG. 1(B). The light transmission film 11-1 can be formed from e.g. a solder resist (or, in a broader sense, a resist).

Although in the example shown in FIG. 4, wiring to the light-emitting part 14 and wiring to the light-receiving part 16 are omitted, the first surface and the second surface of the substrate 11 may be roughened so that the wiring on the substrate 11 do not detach. Therefore, forming the light transmission film 11-1 on the first surface and the second surface of the substrate 11 fills over roughness on the surface of the substrate 11 with the light transmission film and enhances the flatness of the entirety of the substrate 11. In other words, since the light transmission film 11-1 on the substrate 11 is flat, it is possible to reduce diffusion of light off the surface roughness on the substrate 11. In other words, the presence of the light transmission film 11-1 increases the transmittance of the substrate 11. Therefore, the amount of light reaching the light-receiving part 16 or the detection site O is increased, and the detection accuracy of the biological information detector is further increased.

The refraction index of the light transmission film 11-1 is preferably between the refraction index of air and the refraction index of the substrate 11. Also, the refraction index of the light transmission film 11-1 is preferably closer to the refraction index of the substrate 11 than the refraction index of air. In such an instance, it is possible to reduce reflection of light at an interface.

The biological information detector may further contain an infrared cut filter 19-1. The infrared cut filter 19-1 is positioned on a light path from the light-emitting part 14 to the light-receiving part 16. In the example shown in FIG. 4, the infrared cut filter 19-1 is formed on the contact surface of the protecting part 19. The infrared cut filter 19-1 may be configured by e.g. coating the contact surface of the protecting part 19 with a material that absorbs infrared light. In an instance in which the protecting part 19 is made of glass, the protecting part 19 provided with the infrared cut filter 19-1 may be referred to as an infrared-cut glass. The infrared cut filter 19-1 may also be formed not only on the contact surface of the protecting part 19 but on the entirety of an outside surface of the protecting part 19. The infrared cut filter 19-1 may also be formed on the entirety of an inside surface of the protecting part 19. Alternatively, the infrared cut filter 19-1 may be formed on a surface of the substrate 11 or a surface of the light-receiving part 16, instead of the contact surface of the protecting part 19. Since biological substances (water or haemoglobin) readily allows transmission of infrared light, the infrared cut filter 19-1 positioned on the light path from the light-emitting part 14 to the light-receiving part 16 can reduce a noise component arising from external light.

Figure 5:
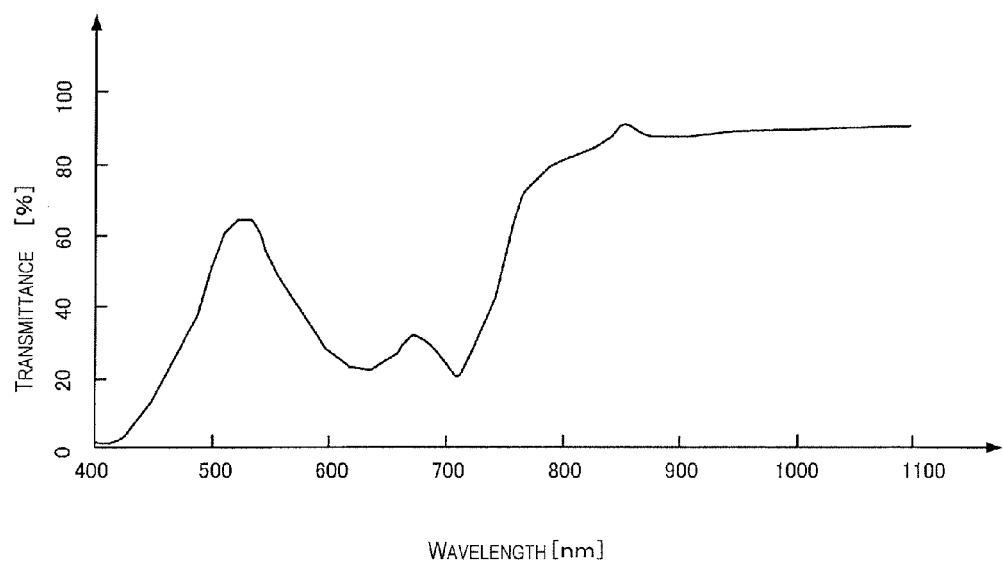
FIG. 5 is an example of transmission characteristics of light passing through a substrate coated with a light transmission film.

FIG. 5 is an example of transmission characteristics of light passing through the substrate 11 coated with the light transmission film 11-1. In the example shown in FIG. 5, transmittance is calculated using the intensity of light before being transmitted through the substrate 11 and the intensity of light after being transmitted through the substrate 11. In the example shown in FIG. 5, in a region of wavelength equal to or less than 700 nm, which is the lower limit of the biological window, the transmittance is at a maximum for light having a wavelength of 525 nm. Or, in the example shown in FIG. 5, in the region of wavelength equal to or less than 700 nm, which is the lower limit of the biological window, the maximum transmittance of light passing through the light transmission film 11-1 falls within a range of ±10% of the maximum intensity of the wavelength of light generated by the light-emitting part 14 in FIG. 2, for example. It is preferable that the light transmission film 11-1 thus selectively transmit light generated by the light-emitting part 14 (e.g. the first light R1 shown in FIG. 1; or specifically, the reflected light R1' produced by the first light R1 being reflected). The presence of the light transmission film 11-1 makes it possible to enhance the flatness of the substrate 11 and prevent, to a certain extent, a decrease in efficiency of the light-emitting part 14 and the light-receiving part 16. In an instance in which transmittance has a maximum value (or in a broader sense, a peak value) within e.g. a visible light region for light having a wavelength of 525 nm, as shown in the example in FIG. 5, the light transmission film 11-1 is e.g. green.

Figure 6:
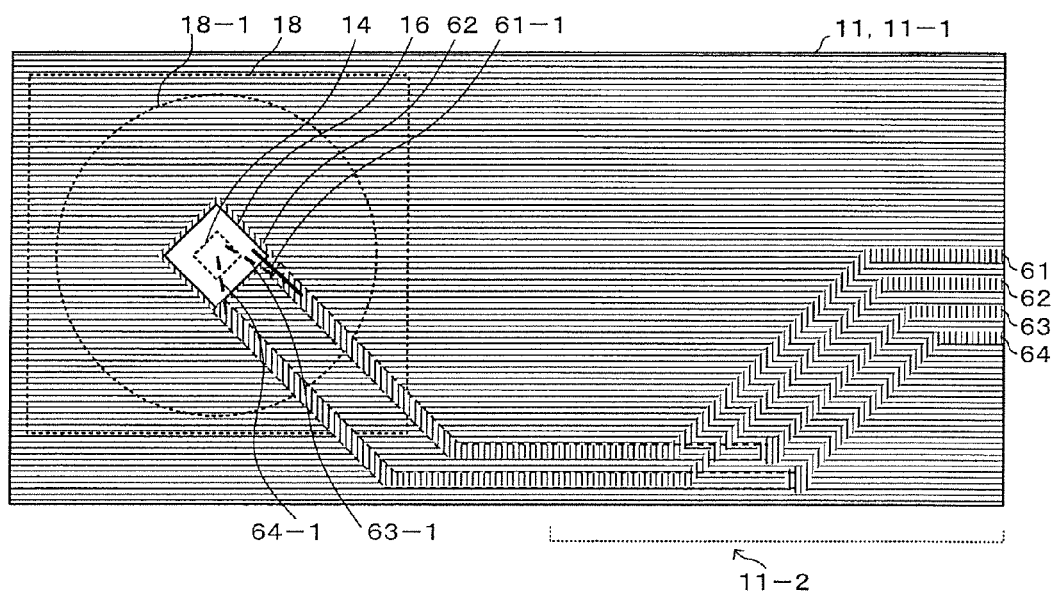
FIG. 6 is an example of an outer appearance of the light transmission film.

FIG. 6 is an example of an outer appearance of the light transmission film 11-1 shown in FIG. 4. As shown in FIG. 6, in plan view (e.g. as viewed from a side towards the light-receiving part 16 in FIG. 4), the substrate 11, on which the light transmission film 11-1 is formed, is rectangular. In the example shown in FIG. 6, the light-receiving part 16 is placed on the first surface (e.g. the front surface) of the substrate 11. The light transmission film 11-1 can be formed on a region of the first surface of the substrate 11 where the light-receiving part 16 is not present.

Specifically, wiring 61 for connecting with e.g. an anode of the light-receiving part 16, and wiring 62 for connecting with e.g. a cathode of the light-receiving part 16, are formed on the first surface of the substrate 11. In the example shown in FIG. 6, the wiring 61 is connected to the anode of the light-receiving part 16 via a bonding wire 61-1, and the wiring 62 is directly connected to the cathode of the light-receiving part 16. The first surface of the substrate 11 can be coated with the light transmission film 11-1 after the wiring 61 and the wiring 62 are formed on the substrate 11. In other words, the light transmission film 11-1 may be formed on top of the wiring 61 and the wiring 62. However, the light transmission film 11-1 may be selectively applied so that only a region of the substrate 11 where the light-receiving part 16, the wiring 61, and the wiring 62 are not provided (i.e., a light transmission region) is coated.

Then, the reflecting part 18 may be formed or secured on the substrate 11 (and the light transmission film 11-1). As shown in FIG. 6, in plan view, the reflecting part 18 has a quadrilateral profile, and a boundary 18-1 between the reflecting surface of the reflecting part 18 (i.e., the dome surface) and the substrate 11 (and the light transmission film 11-1) has a circular profile. The light transmission film 11-1 may also be selectively applied so that only the light transmission region within the boundary 18-1 (i.e., the circle) is coated. In other words, the light transmission film 11-1 may be selectively applied so that only the light transmission region that transmits light reaching the light-receiving part 16 is coated.

In the example shown in FIG. 6, the light-emitting part 14 is placed on the second surface (i.e., the reverse surface) of the substrate 11. As with the first surface, the light transmission film 11-1 may be formed on a region on the second surface of the substrate 11 on which the light-emitting part 14 is not placed. The light transmission film 11-1 is preferably formed on at least a light transmission region (i.e., a light transmission region through which light emitted by the light-emitting part 14 is transmitted). In the example shown in FIG. 6, at an end part 11-2 of the substrate 11, a wiring 63 is formed on the first surface, formed so as to penetrate the substrate 11, and formed on the second surface. At the end part 11-2 of the substrate 11, a wiring 64 is also formed on the first surface, formed so as to penetrate the substrate 11, and formed on the second surface. The wiring 63 is connected on a side of the second surface to a cathode of the light-emitting part 14 via e.g. a bonding wire 63-1, and the welding position 64 is connected on the side of the second surface to an anode of the light-emitting part 14 via e.g. a bonding wire 64-1. The end part 11-2 of the substrate 11 held between the reflecting part 18 and the protecting part 19 is caused to outwardly project, thereby allowing the wiring for the light-emitting part 14 and the light-receiving part 16 to be readily led to the exterior.

Figure 7:
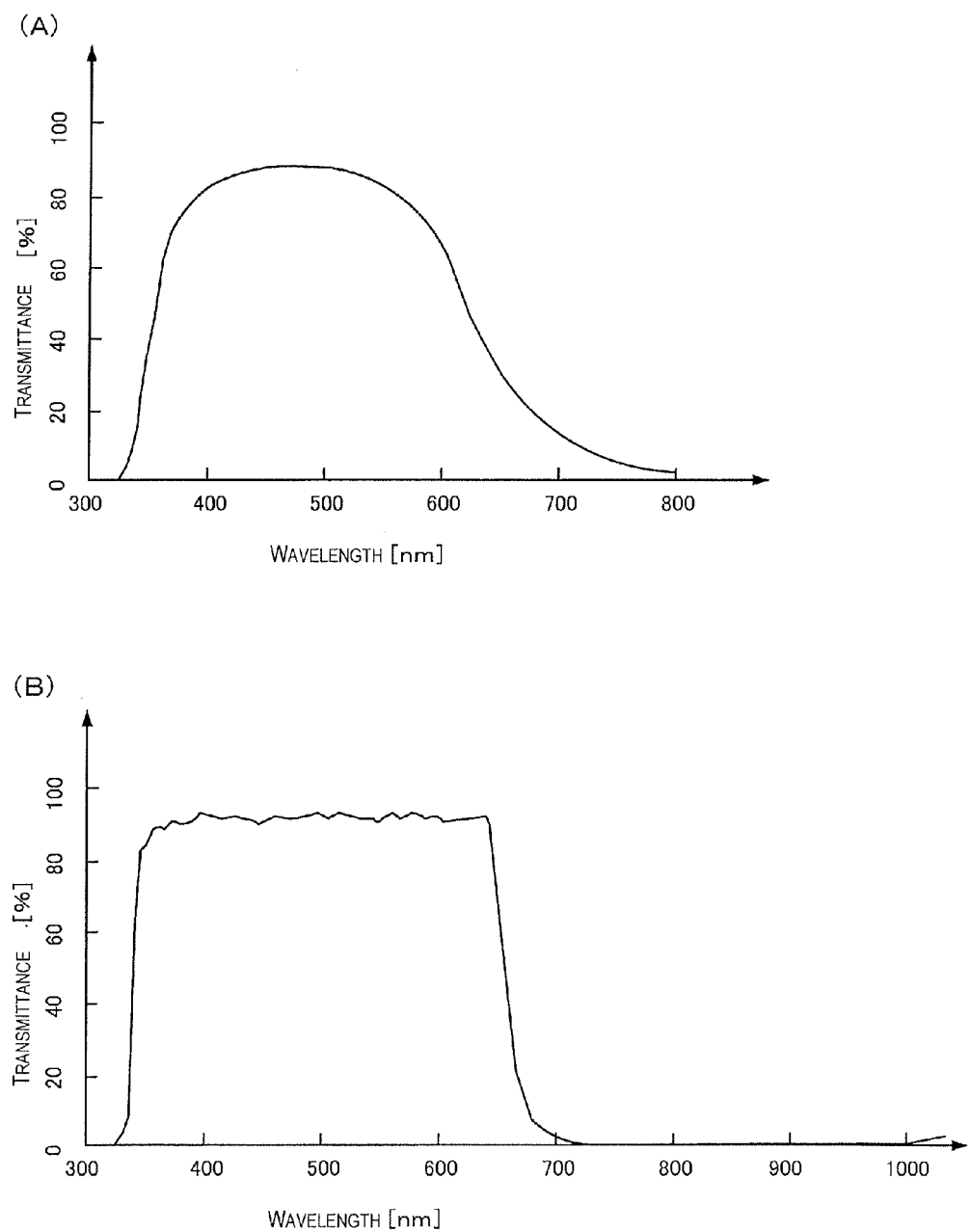
FIGS. 7(A) and 7(B) are schematic diagrams used to describe an infrared cut filter.

FIGS. 7(A) and 7(B) are schematic diagrams used to describe the infrared cut filter 19-1 shown in FIG. 4. FIG. 7(A) shows an example of transmission characteristics of light passing through the protecting part 19 that has not been provided with the infrared cut filter 19-1. FIG. 7(B) shows an example of transmission characteristics of light passing through the infrared-absorbing material forming the infrared cut filter 19-1. FIGS. 7(A) and 7(B) show that the presence of the infrared cut filter 19-1 makes it possible to prevent entry of light (e.g. external light) having a frequency within a range of 700 nm to 1100 nm, known as the biological window. The infrared cut filter 19-1 may instead only prevent entry of light having a frequency within a part of the range of 700 nm to 1100 nm (e.g., 700 nm to 800 nm).

Figure 8:
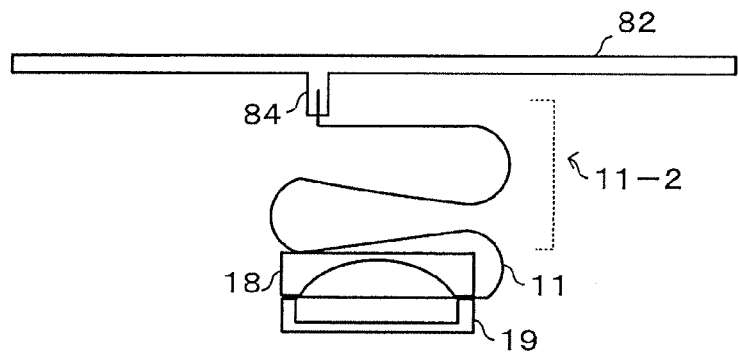
FIG. 8 is an example of the substrate being accommodated.

FIG. 8 shows an example in which the substrate 11 is accommodated. In the example shown in FIG. 8, the substrate 11 is formed from a flexible substrate. Therefore, the end part 11-2 of the substrate 11 is capable of being bent. The substrate 11 may be connected to a motherboard (e.g. a principal substrate forming a biological information measuring device described further below) 82 of a computer in a state in which the end part 11-2 is bent, as shown in FIG. 8. In other words, bending the substrate 11 makes it possible to provide a small biological information detector. The light transmission film 11-1 is omitted from FIG. 8. The light-emitting part 14 and the light-receiving part 16 are also omitted. Wiring for the light-emitting part 14 and wiring for the light-receiving part 16 may be formed on the substrate 11 as shown e.g. in FIG. 6, and each of the wiring is capable of respectively connecting the light-emitting part 14 and the light-receiving part 16 to a control circuit on the motherboard 82 via a connector 84.

The substrate 11 is held between the reflecting part 18 and the protecting part 19, and the reflecting part 18 is thereby secured to the substrate 11. One of either the light-emitting part 14 or the light-receiving part 16 can be positioned in a space formed by the reflecting surface of the reflecting part 18 and the substrate 11. While the substrate 11 where the reflecting part 18 has been secured is locally incapable of being bent, the end part 11-2 of the substrate 11 to which the reflecting part 18 is not secured is capable of being bent. Since the substrate 11 is held between the reflecting part 18 and the protecting part 19, even with the substrate 11 being a flexible substrate that inherently lacks stiffness, the light-emitting part 14 and the light-receiving part 16 can be mounted on the substrate 11 and supported.

Figure 9:
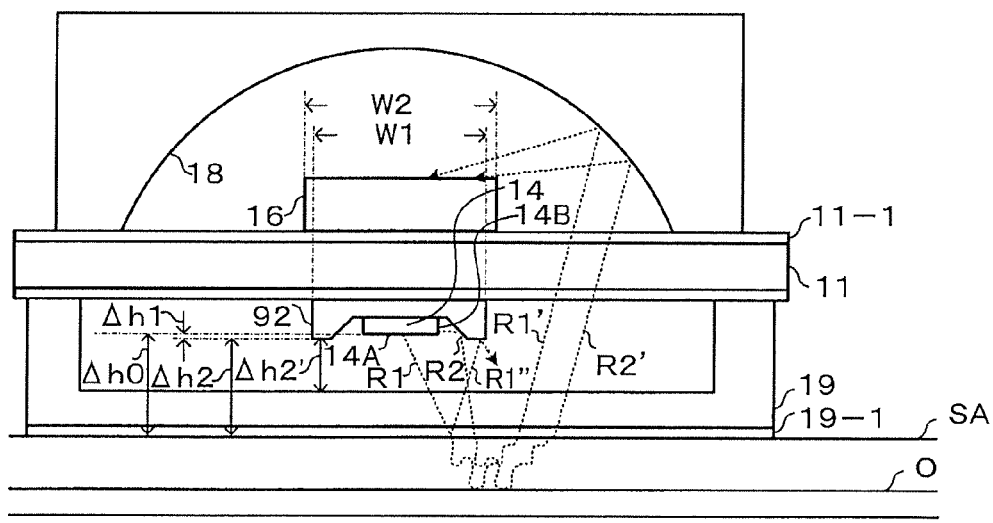
FIG. 9 is an example of another configuration of a biological information detector according to the present embodiment.

FIG. 9 shows another example of a configuration of the biological information detector according to the present embodiment. As shown in FIG. 9, the biological information detector may contain a reflecting part 92 for reflecting light. In the descriptions given below, the reflecting part 92 shall be referred to as a first reflecting part, and the reflecting part 18 such as that shown in FIG. 1(A) shall be referred to as a second reflecting part. In the example shown in FIG. 9, the first reflecting part 92 and the light-receiving part 16 are placed on the substrate 11 after the light transmission film 11-1 is formed on the substrate 11.

In the example shown in FIG. 9, the biological information detector contains the light-emitting part 14, the first reflecting part 92, the light-receiving part 16, and the second reflecting part 18. The light-emitting part 14 emits a first light R1 directed at the detection site O of the examined body (e.g. the user), and a second light R2 directed at a direction other than that of the detection site O (i.e., directed at the first reflecting part 92). The first reflecting part 92 reflects the second light R2 and directs the second light R2 towards the detection site O. The light-receiving part 16 receives lights R1', R2' (i.e., reflected lights), having biological information, the lights R1', R2' produced by each of the first light R1 and the second light R2 being reflected at the detection site O. The second reflecting part 18 reflects the lights R1', R2' having biological information from the detection site O (i.e. the reflected lights) and directs the lights R1', R2' towards the light-receiving part 16. The presence of the first reflecting part 92 causes the light second light R2, that does not directly reach the detection site O of the test subject (i.e., the user), to reach the detection site O. In other words, the amount of light reaching the detection site O via the first reflecting part 92 increases, and the efficiency of the light-emitting part 14 increases. Therefore, the detection accuracy (i.e., the signal-to-noise ratio) of the biological information detector increases.

Figure 16:
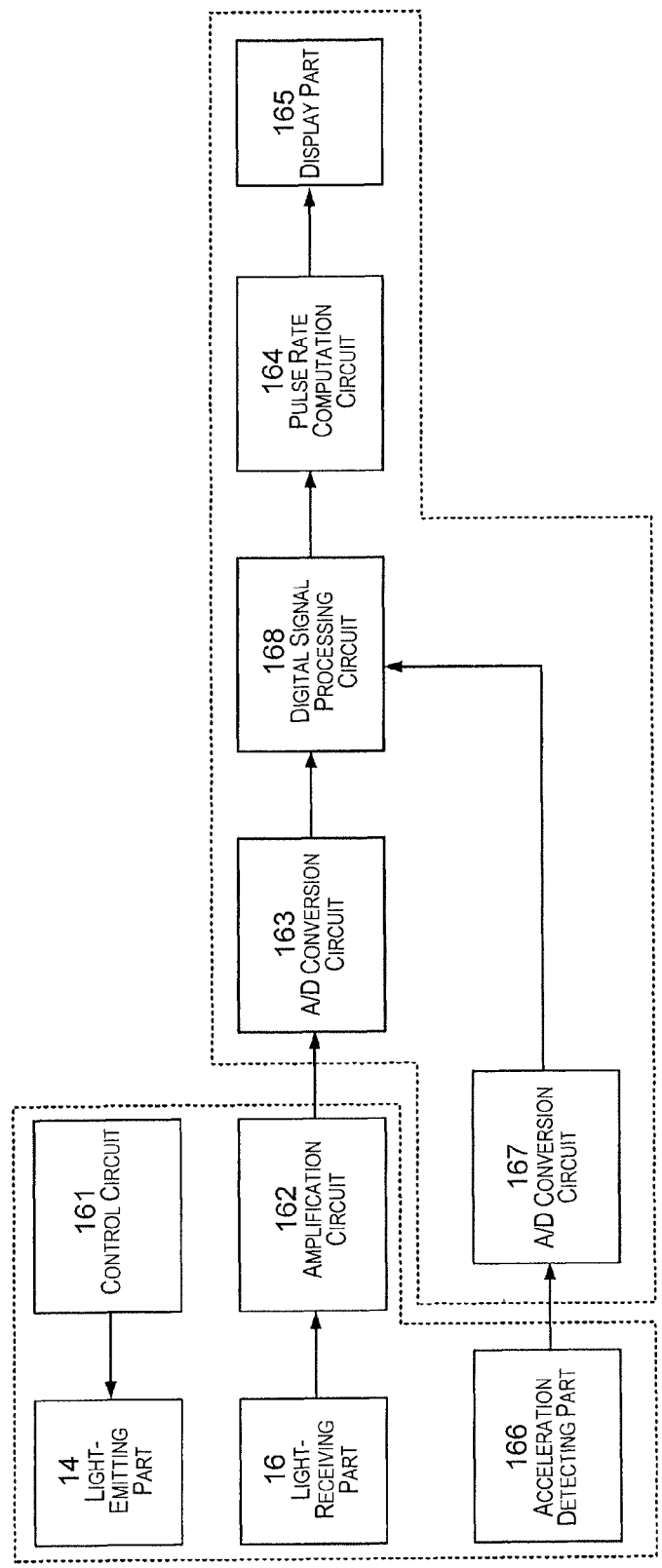
FIG. 16 is an example of a configuration of the biological information measuring device.

In Patent Citation 1, there is disclosed a configuration corresponding to the second reflecting part 18 (i.e., a reflecting part 131 in FIG. 16 of Patent Citation 1). Specifically, the light-receiving part 12 in FIG. 16 of Patent Citation 1 receives light reflected at a detection site via the reflecting part 131. However, in Patent Citation 1, a configuration corresponding to the first reflecting part 92 is not disclosed. In other words, at the time of filing, those skilled in the art had not been aware of the issue of increasing the efficiency of the light-emitting part 11 in FIG. 16 in Patent Citation 1.

In the example shown in FIG. 9, the second light R2 travels into the test subject, and the reflected light R2' reflected at the detection site O travels towards the second reflecting part 18. Biological information (i.e., the pulse rate) is also reflected in the reflected light R2' reflected at the detection site O. In the example shown in FIG. 9, the first light R1 is partially reflected at a surface SA of the test subject (e.g. a skin surface). In an instance in which the detection site O is within the test subject, biological information (i.e., the pulse rate) is not reflected in reflected light R1" reflected at the surface SA of the test subject (i.e., a directly reflected light).

In the example shown in FIG. 9, the light-emitting part 14 may have a first light-emitting surface 14A for emitting the first light R1, the first light-emitting surface 14A facing the detection site O. The light-emitting part 14 may also have a second light-emitting surface 14B for emitting the second light R2, the second light-emitting surface 14B being a side surface of the first light-emitting surface 14A. In such an instance, the first reflecting part 92 may have a wall part surrounding the second light-emitting surface 14B, and the wall part may have a first reflecting surface (corresponding to label 92-2 shown in FIGS. 10(A) through 10(C)) capable of reflecting the second light R2 towards the detection site O. The second light R2 is not necessarily limited to that emitted from the second light-emitting surface 14B. Principally, the first reflecting surface (label 92-2 shown in FIGS. 10(A) through 10(C)) reflects light other than light travelling directly from the light-emitting part 14 to the detection site O (i.e., the second light R2) and directs the second light R2 towards the detection site O.

Figure 10:
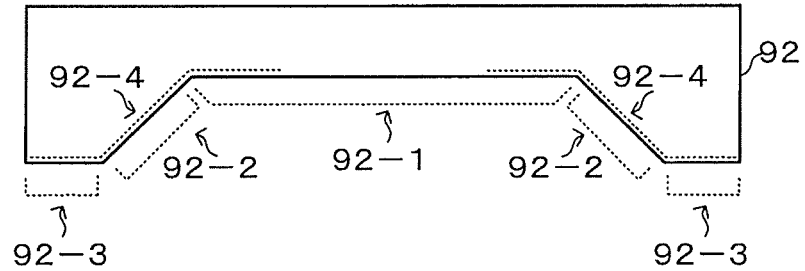
FIGS. 10(A), 10(B), and 10(C) are examples of a configuration of a first reflecting part.
Figure 10:
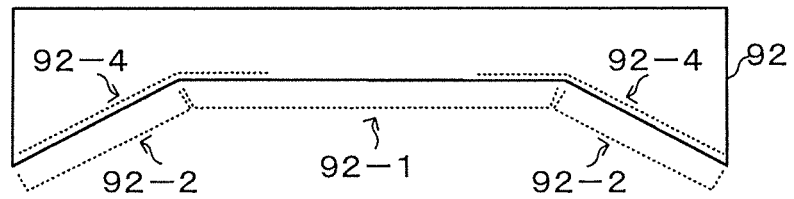
Figure 10:
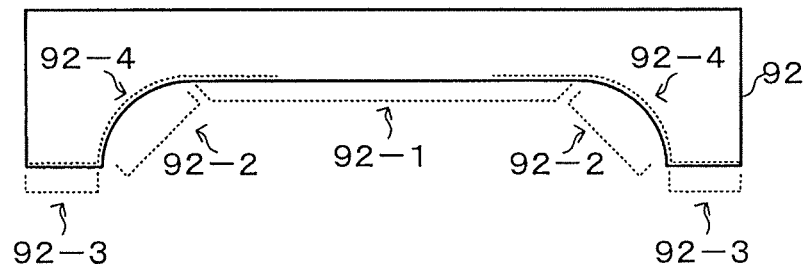

The wall part of the first reflecting part 92 may further have a second reflecting surface (corresponding to 92-3 in FIGS. 10(A) and 10(C)) for reflecting light not having biological information (i.e., invalid light; noise) reflected at the surface of the test subject, thereby minimizing incidence of light not having biological information onto the light-receiving part 16.

The protecting part 19 also makes it possible to ensure that there is a gap between the first reflecting part 92 and the detection site O (e.g. Δh2). There also exists a gap between the first reflecting part 92 and the protecting part 19 (e.g. Δh2').

When, in cross-section view, W1 is a maximum value for the length of the first reflecting part 92 in a direction parallel to the first surface of the substrate 11 and W2 is a maximum value for the length of the light-receiving part 16 in the same direction, an equation is satisfied. The substrate 11 allows transmission of the reflected light R1' produced by the first light R1 emitted at the detection site O, and other light. The maximum value W1 for the length of the first reflecting part 92 is made to be equal to or less than the maximum value W2 for the length of the light-receiving part 16, thereby making it possible to increase the amount of light reaching the second reflecting part 18. In other words, the maximum value W1 for the length of the first reflecting part 92 can be set so that the first reflecting part 92 does not block or reflect the reflected light R1' reflected at the detection site O.

FIGS. 10(A), 10(B), and 10(C) each show an example of a configuration of the first reflecting part 92 shown in FIG. 9. As shown in FIG. 10(A), the first reflecting part 92 may have a support part 92-1 for supporting the light-emitting part 14, and an inner wall surface 92-2 and a top surface 92-3 of the wall part surrounding the second light-emitting surface 14B of the light-emitting part 14. In FIGS. 10(A) through 10(C), the light-emitting part 14 is omitted. In the example shown in FIG. 10(A), the first reflecting part 92 is capable of reflecting the second light R2 towards the detection site O off the inner wall surface 92-2 (see FIG. 9), and has the first reflecting surface on the inner wall surface 92-2. The thickness of the support part 92-1 is e.g. 50 μm to 1000 μm, and the thickness of the top surface 92-3 is e.g. 100 μm to 1000 μm.

In the example shown in FIG. 10(A), the inner wall surface 92-2 has an inclined surface (92-2) which, with increasing distance in a width direction (i.e., a first direction) from a center of the first reflecting part 92, displaces towards the detection site O in a height direction (i.e., a direction that is orthogonal with the first direction), in cross-section view. The inclined surface (92-2) in FIG. 10(A) is formed by, in cross-section view, an inclined plane, but may also be a curved surface shown in e.g. FIG. 10(C), or a similar inclined surface. The inner wall surface 92-2 may also be formed as a plurality of inclined planes whose angle of inclination vary from one another, or by a curved surface having a plurality of curvatures. In an instance in which the inner wall surface 92-2 of the first reflecting part 92 has an inclined surface, the inner wall surface 92-2 of the first reflecting part 92 is capable of reflecting the second light R2 towards the detection site O. In other words, the inclined surface on the inner wall surface 92-2 of the first reflecting part 92 can be said to be the first reflecting surface for improving the directivity of the light-emitting part 14. In such an instance, the amount of light reaching the detection site O increases further. The top surface 92-3 shown in FIGS. 10(A) and 10(C) may be omitted as shown, for example, in FIG. 10(B). In an instance in which the first reflecting part 92 has the top surface 92-3, the reflected light R1" reflected at the surface SA of the test subject (i.e., the directly reflected light) can be reflected towards the detection site O or surroundings thereof, and the reflected light R1" is deterred from reaching the light-receiving part 16 (see FIG. 9). Specifically, the top surface 92-3 shown in FIGS. 10(A) and 10(C) can be said to be the second reflecting surface for reflecting the directly reflected light (or in a broader sense, noise) that would otherwise reach the second reflecting part 18 and the light-receiving part 16, and reducing noise. In FIGS. 10(A) through 10(C), a range indicated by label 92-4 function as a mirror surface part.

In the example shown in FIG. 9, the first reflecting part 92 may project towards the detection site O by e.g. a predetermined height Δh1 (where Δh1 is e.g. 50 μm to 950 μm) in relation to a surface of the light-emitting part 14 that determines the shortest distance relative to the surface SA of the test subject (e.g. the first light-emitting surface 14A). In other words, a spacing between the first reflecting part 92 and the surface SA of the test subject (e.g. Δh2=Δh0−Δh1, where Δh2 is 200 μm to 1200 μm) may be smaller than a spacing that represents the shortest distance between the light-receiving part 14 and the surface SA of the test subject (e.g. Δh0=Δh1+Δh2). Therefore, in the first reflecting part 92, the presence of e.g. a projection Δh1 from the light-emitting part 14 makes it possible to increase the area of the first reflecting surface (92-2) and increase the amount of light reaching the detection site O. Also, with regards to the light reflected at the detection site O, the presence of a space Δh2 between the first reflecting part 92 and the surface SA of the test subject makes it possible to obtain a light path for the light to reach the second reflecting part 18 from the detection site O. Also, in an instance in which the first reflecting part 92 has the second reflecting surface (92-3), adjusting Δh1 and Δh2 allows the amount of light having biological information (i.e., valid light) and light not having biological information (i.e., invalid light: noise) incident on the light-receiving part 16 to be respectively adjusted, thereby making it possible to further improve the S/N.

Figure 11:
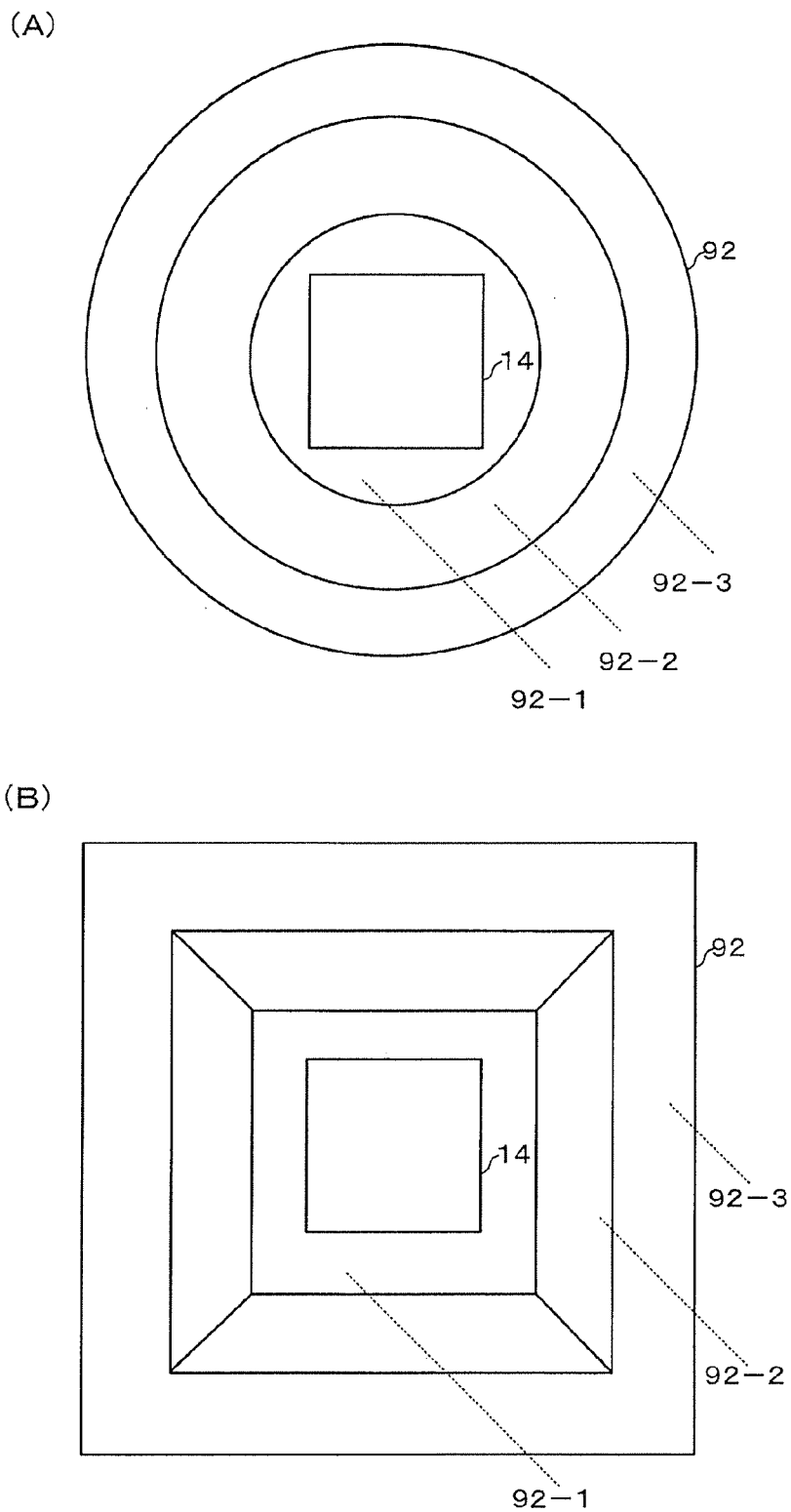
FIGS. 11(A) and 11(B) are examples of an outer appearance of the first reflecting part and the light-emitting part.

FIGS. 11(A) and 11(B) respectively show an example of an outer appearance of the first reflecting part 92 and the light-emitting part 14 of FIG. 9 in plan view. In the example shown in FIG. 11(A), in plan view (when viewed from e.g. towards the detection site O shown in FIG. 9), an outer circumference of the first reflecting part 92 is circular, where the diameter of the circle is e.g. 200 μm to 11,000 μm. In the example shown in FIG. 11(A), the wall part (92-2) of the first reflecting part 92 surround the light-emitting part 14 (see FIGS. 9 and 10(A)). The outer circumference of the first reflecting part 92 may also be a quadrilateral (or specifically, a square) in plan view as shown e.g. in FIG. 11(B). Also, in the examples shown in FIGS. 11(A) and 11(B), in plan view (when viewed from e.g. towards the detection site O shown in FIG. 9), the outer circumference of the light-emitting part 14 is a quadrilateral (or specifically, a square), where the length of one side of the square is e.g. 100 μm to 10,000 μm. The outer circumference of the light-emitting part 14 may also be circular.

The first reflecting part 92 is made of metal whose surface is subjected to mirror surface finishing, and thereby has a reflective structure (or specifically, a mirror reflection structure). The first reflecting part 92 may also be formed from e.g. a resin whose surface is subjected to mirror surface finishing. Specifically, for example, a base metal forming a base of the first reflecting part 92 is readied, and a surface of the base metal is then e.g. subjected to plating. Alternatively, a mold of the first reflecting part 92 (not shown) is filled with a thermoplastic resin, molding is performed, and a metal film, for example, is then deposited by vapor deposition on a surface of the mold.

In the examples shown in FIGS. 11(A) and 11(B), in plan view (when viewed from e.g. towards the detection site O shown in FIG. 9), a region of the first reflecting part 92 other than that directly supporting the light-emitting part 14 (the inner wall surface 92-2 and the top surface 92-3, and a part of the support part 92-1) is exposed. The exposed region is shown as a mirror surface part 92-4 in FIG. 10(A). Although in the example shown in FIG. 10(A), a dotted line representing the mirror surface part 92-4 is shown within the first reflecting part 92, the mirror surface part 92-4 is actually formed on a surface of the first reflecting part 92.

In the examples shown in FIGS. 10(A), 10(B), and 10(C), the mirror surface part 92-4 preferably has a high reflectivity. The reflectivity of the mirror surface part 92-4 is e.g. 80% to 90% or higher. It is possible for the mirror surface part 92-4 to be formed only on the inclined surface of the inner wall surface 92-2. In an instance in which the mirror surface part 92-4 is formed not only on the inclined surface of the inner wall surface 92-2 but also on the support part 92-1, the directivity of the light-emitting part 14 increases further. In an instance in which the mirror surface part 92-4 is formed on the top surface 92-3, the first reflecting part 12 is capable of reflecting the reflected light R1", which has been reflected in the surface SA of the test subject (i.e., the directly reflected light; invalid light), towards the detection site O or the surroundings thereof, as shown e.g. on FIG. 9, and the reflected light R1" is deterred from reaching the second reflecting part 18 and the light-receiving part 16. Since the directivity of the light-emitting part 14 increases and the directly reflected light (or in a broader sense, noise) decreases, the detection accuracy of the biological information detector increases.

Figure 12:
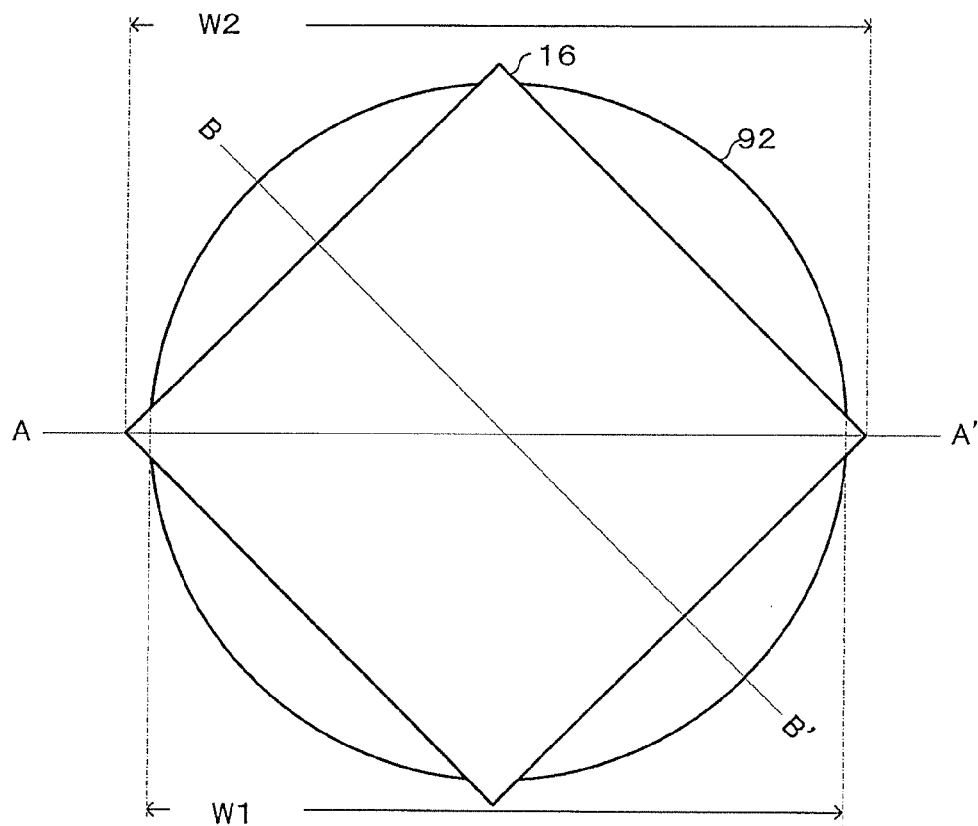
FIG. 12 is an example of an outer appearance of the light-receiving part.

FIG. 12 shows an example of an outer appearance of the light-receiving part 16 in FIG. 9. In the example shown in FIG. 12, in plan view (e.g. when viewed from a side towards the second reflecting part 18 in FIG. 9), an outer circumference of the light-receiving part 16 is a quadrilateral (or specifically, a square), and one side of the square is e.g. 100 µm to 10,000 µm. An outer circumference of the first reflecting part 92 is, in plan view (e.g. when viewed from a side towards the second reflecting part 18 in FIG. 9), circular. The outer circumference of the first reflecting part 92 may instead be a quadrilateral (or specifically, a square), as in the example shown in FIG. 11(B). The outer circumference of the light-receiving part 16 may also be circular.

In the example shown in FIG. 12, as shown by line segment A-A', when W1 is a maximum value for the length of the first reflecting part 92 and W2 is a maximum value for the length of the light-receiving part 16, an equation $W1 \leq W2$ is satisfied. A cross-section view along the line segment A-A' in FIG. 12 corresponds to FIG. 9. In a cross-section view along line segment B-B' in FIG. 9, the maximum value W1 of the length of the first reflecting part 92 is larger than a minimum value of the length of the light-receiving part 16. Although the maximum value W1 of the length of the first reflecting part 92 may be set so as to be equal to or smaller than the minimum value of the length of the light-receiving part 16, the efficiency of the first reflecting part 92 (or, in a broader sense, the efficiency of the light-emitting part 14) would decrease. In the example shown in FIG. 12, the maximum value W1 of the length of the first reflecting part 92 is set to be equal or smaller than the maximum value W2 of the length of the light-receiving part 16, and the maximum value W1 of the length of the first reflecting part 92 is set to be larger than the minimum value of the length of the light-receiving part 16, so that the efficiency of the light-emitting part 14 can be maintained without blocking or reflecting the reflected light R1'.

Figure 13:
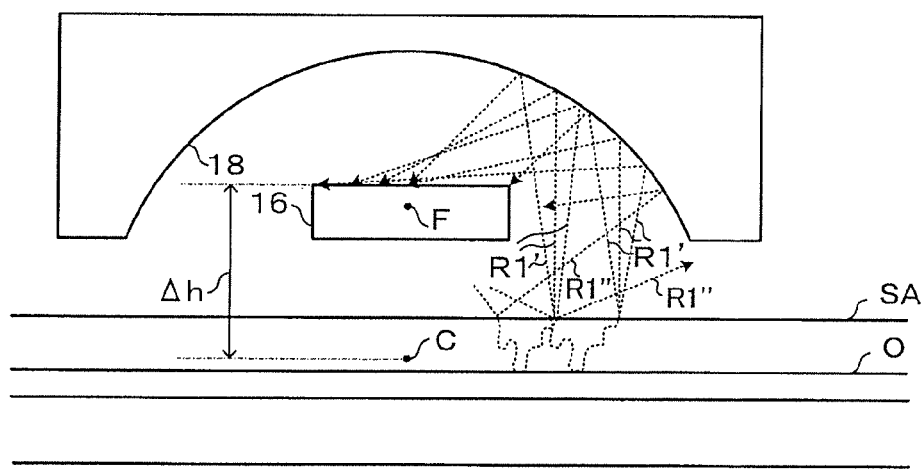
FIG. 13 is a schematic diagram showing a setting position of a second reflecting part.

FIG. 13 is a schematic diagram showing a setting position of the second reflecting part 18 in FIG. 9 (or FIG. 1). The reflecting surface of the second reflecting part 18 may be formed as e.g. a spherical surface (or in a broader sense, a dome surface), so that the reflected light R1', produced by the first light R1 being reflected at the detection site O, is reflected towards the light-receiving part 16. As shown in FIG. 13, in cross-section view, the reflecting surface of the second reflecting part 18 is an arc. The radius of the arc is e.g. 1000 µm to 15,000 µm. A center C of the arc that defines the spherical surface is located within the test subject. In an instance in which the detection site O is located within the test subject, the reflected light R1" reflected at the surface SA of the test subject is an invalid light not having biological information. The inventors identified that in an instance in which the reflecting surface of the second reflecting part 18 is formed by a spherical surface and the center C of the arc that defines the spherical surface, the second reflecting part 18 minimizes reflected light reflected at the surface SA of the test subject (or in a broader sense, noise). In FIG. 13, the distance between the light-receiving surface of the light-receiving part 16 and the center C of the arc that defines the spherical surface is represented by Δh.

The reflecting surface of the second reflecting part 18 may also be formed by a parabolic surface (or in a broader sense, a dome surface) instead of the spherical surface. As shown in FIG. 13, in cross-section view, the reflecting surface of the second reflecting part 18 is an arc, but may be a parabolic line instead of an arc. If the reflecting surface of the second reflecting part 18 is a parabolic surface, the focus of the parabolic line defining the parabolic surface is shown in FIG. 13 by the letter F. The focus F of the parabolic line defining the parabolic surface is located towards the test subject relative to the light-receiving surface of the light-receiving part 16. Light that travels perpendicular to the surface SA of the test subject reflects at the reflecting surface of the second reflecting part 18 (i.e., the parabolic surface) and collects at the focus F of the parabolic line defining the parabolic surface. Therefore, the focus F being located so as to not coincide with the light-receiving surface of the light-receiving part 16 results in a greater likelihood of light having a path that is nearly perpendicular to the surface SA of the test subject (e.g. the reflected light R1' produced by reflection of the first light R1; valid light) collecting on the light-receiving surface of the light-receiving part 16.

The second reflecting part 18 is formed from e.g. a resin, whose surface (i.e., the reflecting surface facing the light-receiving part 16) is subjected to mirror surface finishing, and thereby has a reflective structure (or specifically, a mirror reflection structure). In other words, the second reflecting part 18 is capable of causing mirror reflection of light without causing diffuse reflection of light. In an instance in which the second reflecting part 18 has a mirror reflection structure, the second reflecting part 18 is also capable of not causing the reflected light R1" (i.e., the directly reflected light) to reflect towards the light-receiving part 16, where the reflected light R1" produced by reflection of the first light R1 has a reflection angle that is different to that of the reflected light R1' produced by reflection of the first light R1, In such an instance, the detection accuracy of the biological information detector further increases. As shown in FIG. 13, since the reflected light R1' produced by reflection of the first light R1 originates from the detection site O that is within the test subject, the reflection angle of the reflected light R1' produced by reflection of the first light R1 (i.e., a reflection angle relative to a straight line perpendicular to the surface SA of the test subject) is generally small. Meanwhile, since the reflected light R1" produced by reflection of the first light R1 originates from the surface SA of the test subject, the reflection angle of the reflected light R1" produced by reflection of the first light R is generally large.

In FIG. 16 of Patent Citation 1, there is disclosed a reflecting part 131, and according to paragraphs [0046], [0059], and [0077] in Patent Citation 1, the reflecting part 131 has a diffuse reflection structure, and the reflectivity is increased to increase the efficiency of the first reflecting part 12. However, at the time of filing, it had not been recognized by those skilled in the art that in the reflecting part 131 according to Patent Citation 1, directly reflected light (or in a broader sense, noise) is also reflected towards the first reflecting part 12. In other words, the inventors identified that reducing a noise component arising from the directly reflected light from a light reception signal increases the efficiency of the light-receiving part. Specifically, the inventors identified that the detection accuracy of the biological information detector is further increased in an instance in which the second reflecting part 18 has a mirror reflection structure.

Figure 14:
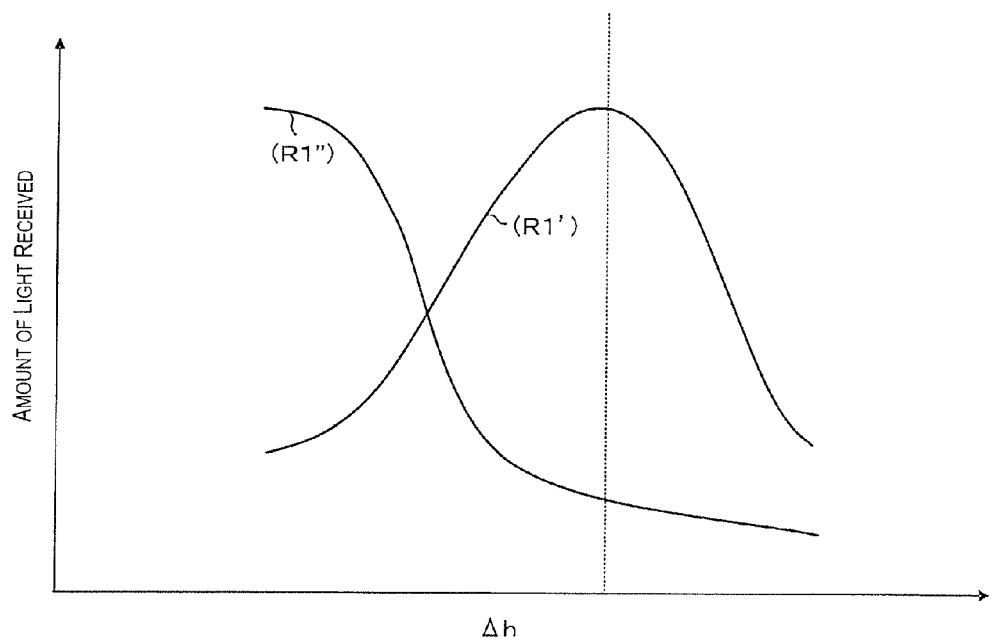
FIG. 14 is a diagram showing a relationship between the setting position of the second reflecting part and the amount of light received at the light-receiving part.

FIG. 14 is a diagram showing a relationship between the setting position of the second reflecting part 18 and the amount of light received at the light-receiving part 16 in FIG. 13 et al. As shown in FIG. 14, with increasing distance Ah between the light-receiving surface of the light-receiving part 16 and the center C of the arc defining the spherical surface, the amount of directly reflected light reflected at the surface SA of the test subject (or, in a broader sense, noise corresponding to the reflected light R1", for example) decreases, while light reflected at the detection site O (or, in a broader sense, biological information corresponding to reflected light R1', for example) increases and then decreases. The position of the Ah can accordingly be optimized. In an instance in which the reflecting surface of the second reflecting part 18 is a parabolic surface, the distance between the light-receiving part of the light-receiving part 16 and the focus F of the parabolic line defining the parabolic surface can also be optimized.

2. Biological Information Measuring Device

Figure 15:
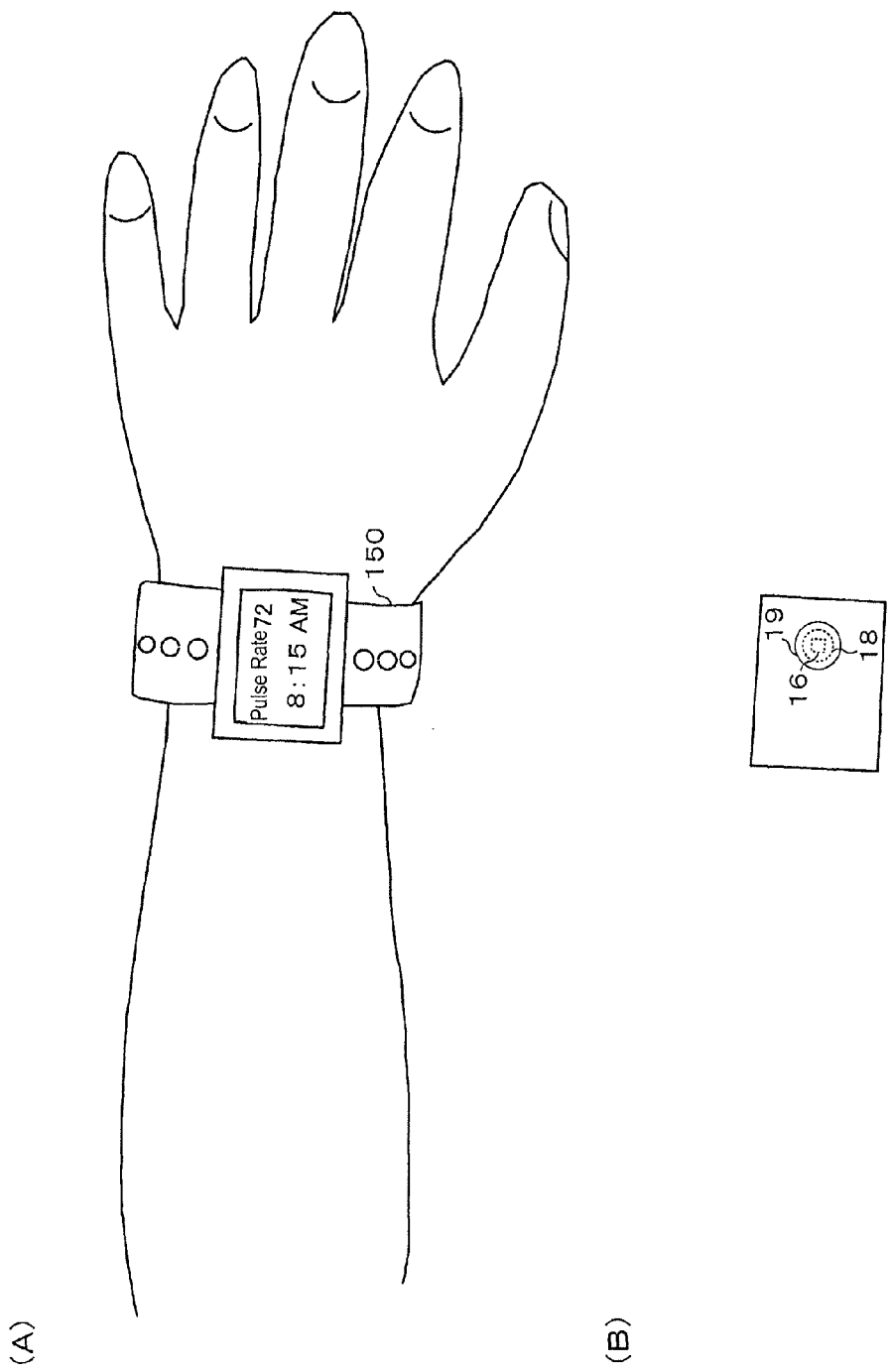
FIGS. 15(A) and 15(B) are examples of an outer appearance of a biological information measuring device containing the biological information detector.

FIGS. 15(A) and 15(B) are examples of outer appearances of a biological information measuring device containing the biological information detector such as that shown in FIG. 1. As shown in FIG. 15(A), the biological information detector shown in FIG. 1, for example, may further contain a wristband 150 capable of attaching the biological information detector to an arm (or specifically, a wrist) of the test subject (i.e., the user). In the example shown in FIG. 15(A), the biological information is the pulse rate indicated by e.g. "72." The biological information detector is installed in a watch showing the time (e.g. "8:15 am"). As shown in FIG. 15(B), an opening part is provided to a back cover of the watch, and the protecting part 19 shown in FIG. 1, for example, is exposed in the opening part. In the example shown in FIG. 15(B), the second reflecting part 18 and the light-receiving part 16 are installed in a watch. In the example shown in FIG. 15(B), the first reflecting part 92, the light-emitting part 14, the wristband 150, and other components are omitted.

FIG. 16 is an example of a configuration of the biological information measuring device. The biological information measuring device includes the biological information detector as shown e.g. in FIG. 1, and a biological information measuring part for measuring biological information from a light reception signal generated at the light-receiving part 16 of the biological information detector. As shown in FIG. 16, the biological information detector may have a light-emitting part 14 and a control circuit 161 for controlling the light-emitting part 14. The biological information detector may further have an amplification circuit 162 for amplifying the light reception signal from the light-receiving part 16. The biological information measuring part may have an A/D conversion circuit 163 for performing A/D conversion of the light reception signal from the light-receiving part 16, and a pulse rate computation circuit 164 for computationally obtaining the pulse rate. The biological information measuring part may further have a display part 165 for displaying the pulse rate.

The biological information detector may have an acceleration detecting part 166, and the biological information measuring part may further have an A/D conversion circuit 167 for performing A/D conversion of a light reception signal from the acceleration detecting part 166 and a digital signal processing circuit 168 for processing a digital signal. The configuration of the biological information measuring device is not limited to that shown in FIG. 16. The pulse rate computation circuit 164 in FIG. 16 may be e.g. an MPU (i.e., a micro processing unit) of an electronic device installed with the biological information detector.

The control circuit 161 in FIG. 16 drives the light-emitting part 14. The control circuit 161 is e.g. a constant current circuit, delivers a predetermined voltage (e.g. 6 V) to the light-emitting part 14 via a protective resistance, and maintains a current flowing to the light-emitting part 14 at a predetermined value (e.g. 2 mA). The control circuit 161 is capable of driving the light-emitting part 14 in an intermittent manner (e.g. at 128 Hz) in order to reduce consumption current. The control circuit 161 is formed on e.g. the motherboard 82 shown in FIG. 8, and wiring between the control circuit 161 and the light-emitting part 14 is formed e.g. on the substrate 11 shown in FIG. 1.

The amplification circuit 162 shown in FIG. 16 is capable of removing a DC component from the light reception signal (i.e., an electrical current) generated in the light-receiving part 16, extracting only an AC component, amplifying the AC component, and generating an AC signal. The amplification circuit 162 removes the DC component at or below a predetermined wavelength using e.g. a high-pass filter, and buffers the AC component using e.g. an operational amplifier. The light reception signal contains a pulsating component and a body movement component. The amplification circuit 162 and the control circuit 161 are capable of feeding a power supply voltage for operating the light-receiving part 16 at e.g. reverse bias to the light-receiving part 16. In an instance in which the light-emitting part 14 is intermittently driven, the power supply to the light-receiving part 16 is also intermittently fed, and the AC component is also intermittently amplified. The amplification circuit 162 is formed on e.g. the mother board 82 shown in FIG. 8, and wiring between the amplification circuit 162 and the light-receiving part 16 is formed on e.g. the substrate 11 shown in FIG. 1. The amplification circuit 162 may also have an amplifier for amplifying the light reception signal at a stage prior to the high-pass filter. In an instance in which the amplification circuit 162 has an amplifier, the amplifier is formed e.g. on the end part 11-2 of the substrate 11 shown in FIG. 6.

The A/D conversion circuit 163 shown in FIG. 16 converts an AC signal generated in the amplification circuit 162 into a digital signal (i.e., a first digital signal). The acceleration detecting part 166 shown in FIG. 16 calculates e.g. gravitational acceleration in three axes (i.e., x-axis, y-axis, and z-axis) and generates an acceleration signal. Movement of the body (i.e., the arm), and therefore the movement of the biological information measuring device, is reflected in the acceleration signal. The A/D conversion circuit 167 shown in FIG. 16 converts the acceleration signal generated in the acceleration detecting part 166 into a digital signal (i.e., a second digital signal).

The digital signal processing circuit 168 shown in FIG. 16 uses the second digital signal to remove or reduce the body movement component in the first digital signal. The digital signal processing circuit 168 may be formed by e.g. an FIR filter or another adaptive filter. The digital signal processing circuit 168 inputs the first digital signal and the second digital signal into the adaptive filter and generates a filter output signal in which noise has been removed or reduced.

The pulse rate computation circuit 164 shown in FIG. 16 uses e.g. fast Fourier transform (or in a broader sense, discrete Fourier transform) to perform a frequency analysis on the filter output signal. The pulse rate computation circuit 164 identifies a frequency that represents a pulsating component based on a result of the frequency analysis, and computationally obtains a pulse rate.

Although a detailed description was made concerning the present embodiment as stated above, persons skilled in the art should be able to easily understand that various modifications are possible without substantially departing from the scope and effects of the present invention. Accordingly, all of such examples of modifications are to be included in the scope of the present invention. For example, terms stated at least once together with different terms having broader sense or identical sense in the specification or drawings may be replaced with those different terms in any and all locations of the specification or drawings.

The entire disclosure of Japanese Patent Application No. 2010-000452, filed Jan. 5, 2010 is expressly incorporated by reference herein.

What is claimed is:

1. A biological information detector comprising:
   a light-emitting part configured to emit a light directed at a detection site of a test subject;
   a light-receiving part configured to receive the light after being reflected at the detection site, the light including biological information;
   a reflecting part configured to reflect the light including the biological information;
   a protecting part configured to protect the light-emitting part; and
   a substrate being in contact with both the reflecting part and the protecting part, and being held by both the reflecting part and the protecting part therebetween, the light-emitting part being positioned on a side of the substrate towards the protecting part, the light-receiving part being positioned on a side of the substrate towards the reflecting part,
   the protecting part including a surface configured to be in contact with the test subject;
   the substrate being made of a material that is transparent with respect to the light including the biological information.

2. The biological information detector according to claim 1, wherein
   the substrate has a first surface corresponding to a light transmission region, and a second surface that is opposite the second surface; and
   a light transmission film is formed on at least one of the first surface and the second surface.

3. The biological information detector according to claim 2, wherein
   the light transmission film is configured to allow selective transmission of light emitted by the light-emitting part.

4. The biological information detector according to claim 1, wherein
   the reflecting part is secured to the substrate;
   the substrate is a flexible substrate; and
   an end part of the substrate is bendable.

5. A biological information detector comprising:
   a light-emitting part configured to emit a light directed at a detection site of a test subject;
   a light-receiving part configured to receive the light after being reflected at the detection site, the light including biological information;
   a reflecting part configured to reflect the light including the biological information;
   a protecting part configured to protect the light-emitting part;
   a substrate being in contact with both the reflecting part and the protecting part, and being held by both the reflecting part and the protecting part therebetween, the light-emitting part being positioned on a side of the substrate towards the protecting part, the light-receiving part being positioned on a side of the substrate towards the reflecting part; and
   an infrared cut filter,
   the protecting part including a contact surface configured to be in contact with the test subject;
   the substrate being made of a material that is transparent with respect to the light including the biological information.

6. The biological information measuring device according to claim 5, wherein
   the infrared cut filter is disposed at least on the contact surface of the protecting part.

7. The biological information detector according to claim 1, further comprising
   a wristband for the biological information detector to be attached to an arm of the test subject.

8. A biological information measuring device comprising:
   the biological information detector according to claim 1; and
   a biological information measuring part subjected to measure biological information from a light reception signal generated at the light-receiving part.

9. The biological information measuring device according to claim 8, wherein
   the biological information is a pulse rate.

* * * * *